(12) United States Patent
Chang (10) Patent No.: US 11,507,139 B2
(45) Date of Patent: Nov. 22, 2022

(54) WEARABLE DEVICE FOR ASSISTING BODY MOVEMENT

(71) Applicant: CHUNG-ANG UNIVERSITY INDUSTRY ACADEMIC COOPERATION FOUNDATION, Seoul (KR)

(72) Inventor: Seung Hwan Chang, Seoul (KR)

(73) Assignee: CHUNG-ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 17/571,827

(22) Filed: Jan. 10, 2022

(65) Prior Publication Data
US 2022/0221899 A1 Jul. 14, 2022

(30) Foreign Application Priority Data
Jan. 11, 2021 (KR) .................. 10-2021-0003039

(51) Int. Cl.
*G06F 1/16* (2006.01)
*G06F 3/01* (2006.01)
(Continued)

(52) U.S. Cl.
CPC ............ *G06F 1/163* (2013.01); *A61B 5/1107* (2013.01); *A61B 5/256* (2021.01); *A61B 5/268* (2021.01); *G06F 3/014* (2013.01)

(58) Field of Classification Search
CPC ....... G06F 1/163; G06F 3/014; A61B 5/1107; A61B 5/256; A61B 5/268; A61B 2562/0261; A61B 2562/0285; A61B 5/1121; A61B 5/6833; A61B 5/1126; A61B 5/263; A61B 5/389; A61B 5/4851; B25J 9/02; B25J 9/1694; A61F 2/72;
(Continued)

(56) References Cited

U.S. PATENT DOCUMENTS 9,797,791 B2 * 10/2017 Vogt .......................... G01L 1/02
9,841,331 B2 * 12/2017 Wood ................... A61B 5/1036
(Continued)

FOREIGN PATENT DOCUMENTS

KR 10-0902081 B1 6/2009
KR 10-2028209 B1 11/2019

*Primary Examiner* — Ibrahim A Khan
(74) *Attorney, Agent, or Firm* — The PL Law Group, PLLC (57) ABSTRACT

A wearable device for assisting a human body movement according to an embodiment of the present disclosure includes a sensor including an inner electrode arranged at a center of an arbitrary circle, a plurality of outer electrodes arranged at regular intervals in a circumferential direction at positions spaced apart from the inner electrode in a radial direction so as to be arranged on a circumference of the circle, and a plurality of deformation elements disposed between the inner electrode and each of the outer electrodes and formed of a material whose resistance is changed by deformation; a controller configured to apply different control signals to an actuator according to a combination of different resistance values of the deformation elements of the sensor; and the actuator operating based on the control signals of the controller.

7 Claims, 7 Drawing Sheets

(51) Int. Cl.
*A61B 5/268* (2021.01)
*A61B 5/256* (2021.01)
*A61B 5/11* (2006.01)

(58) Field of Classification Search
CPC ..... A61F 2/583; A61F 2002/704; A61H 3/00; A61H 2201/50
See application file for complete search history.

(56) References Cited

U.S. PATENT DOCUMENTS

| | | | | |
|---|---|---|---|---|
| 10,240,622 | B1* | 3/2019 | Lindsay | F16K 31/12 |
| 2009/0309579 | A1* | 12/2009 | Cochran | A61B 5/113 |
| | | | | 324/207.16 |
| 2014/0375465 | A1* | 12/2014 | Fenuccio | A61B 5/681 |
| | | | | 361/679.01 |
| 2015/0019135 | A1* | 1/2015 | Kacyvenski | A61B 5/389 |
| | | | | 702/19 |
| 2015/0054728 | A1* | 2/2015 | Choi | G06F 3/017 |
| | | | | 345/156 |
| 2015/0248159 | A1* | 9/2015 | Luo | G06F 1/163 |
| | | | | 427/117 |
| 2015/0309563 | A1* | 10/2015 | Connor | A61B 5/1071 |
| | | | | 73/865.4 |
| 2016/0250015 | A1* | 9/2016 | Kim | A61F 2/105 |
| | | | | 623/15.12 |
| 2016/0313798 | A1* | 10/2016 | Connor | G06F 3/017 |
| 2017/0168565 | A1* | 6/2017 | Cohen | A61B 5/0022 |
| 2017/0215495 | A1* | 8/2017 | Okumiya | A41D 19/0013 |
| 2018/0235293 | A1* | 8/2018 | Lee | B32B 25/20 |
| 2018/0283844 | A1* | 10/2018 | Kamakura | G01B 7/18 |
| 2018/0307314 | A1* | 10/2018 | Connor | A61B 5/1123 |
| 2018/0335842 | A1* | 11/2018 | Rubin | G06F 3/0233 |
| 2020/0026352 | A1* | 1/2020 | Wang | G06F 3/044 |
| 2020/0404994 | A1* | 12/2020 | Yoon | A61B 5/296 |
| 2020/0413533 | A1* | 12/2020 | Majidi | G06F 1/1658 |
| 2021/0002816 | A1* | 1/2021 | Doshi | D06M 11/74 |
| 2021/0124417 | A1* | 4/2021 | Ma | G06F 3/0484 |
| 2021/0330261 | A1* | 10/2021 | Jung | A61B 5/14552 |
| 2022/0087565 | A1* | 3/2022 | Loh | A61B 5/4585 |

* cited by examiner

(THUMB)

(a)

(INDEX FINGER)

(b)

(MIDDLE FINGER)

(c)

(RING FINGER)

(d)

(LITTLE FINGER)

WEARABLE DEVICE FOR ASSISTING BODY MOVEMENT

CROSS-REFERENCE TO RELATED APPLICATION AND CLAIM OF PRIORITY

This application claims priority to Korean Patent Application No. 10-2021-0003039 filed on Jan. 11, 2021 in the Korean Intellectual Property Office (KIPO), the entire disclosures of which are incorporated by reference herein.

BACKGROUND

1. Field

The present disclosure relates to a wearable device for assisting a human body movement, and more particularly, to a wearable device for assisting a human body movement, which is improved to assist a human body movement by precisely sensing deformation of muscles or skin moving in various directions by using a minimum number of sensors.

2. Description of the Related Art

Carbon nanotubes are minute molecules with a diameter of 1 nanometer (1 nanometer is one billionth of a meter) in which carbons connected in hexagonal rings form a long tube. Carbon nanotubes, which are cylindrical carbon crystals with a diameter of 5 nm to 10 nm, are attracting attention as a next-generation high-tech material because of their high tensile strength and high electrical conductivity, and the strength of carbon nanotubes is 100 times superior to steel. These carbon nanotubes have attracted attention as a next-generation semiconductor material as it has been found that they have the properties of being either a conductor or a semiconductor depending on the size of the diameter of carbon nanotubes, and have been widely used, as a versatile material, in various fields such as semiconductors, flat panel displays, fuel cells, super-strong fibers, and biosensors.

Technologies have been developed to align these carbon nanotubes in one direction and use them as sensors. However, only unidirectional sensing is not useful, so there is a need to develop technologies capable of replacing, for example, a relatively expensive Rosette strain gage, by enabling sensing by 360 degrees in various directions.

Recently, research and development on sensor technology for measuring a movement state of a human body and bio-signals by attaching a sensor to the human body has been actively conducted. However, most developed sensor technologies are to attach at least three or more common unidirectional sensors in each of multiple directions to measure a body movement state or bio-signals, and accordingly there is a need for development of a technology of enabling multidirectional sensing with one sensor and assisting a human body movement by using the sensor.

SUMMARY

Provided is a wearable device for assisting a human body movement, which can assist the human body movement by precisely sensing deformation of muscles or skin moving in various directions by using a minimum number of sensors.

Provided is a wearable device for assisting a human body movement, which is used in wearable devices to measure bio-signals, sense a movement state of a human body with high sensitivity in real time, and precisely implement various movements of the human body, based on a signal corresponding to a result of the sensing.

A wearable device for assisting a human body movement includes a sensor including an inner electrode arranged at a center of an arbitrary circle, a plurality of outer electrodes arranged at regular intervals in a circumferential direction at positions spaced apart from the inner electrode in a radial direction so as to be arranged on a circumference of the circle, and a plurality of deformation elements disposed between the inner electrode and each of the outer electrodes and formed of a material whose resistance is changed by deformation; a controller configured to apply different control signals to an actuator according to a combination of different resistance values of the deformation elements of the sensor; and the actuator operating based on the control signals of the controller.

The sensor may further include a base member which is attached to a human body and on which the inner electrode, the outer electrodes, and the deformation elements are placed.

Each of the deformation elements may be a carbon nanotube (CNT) unit in which CNT monomers are connected to each other.

The wearable device may further include an object driven by the actuator, and the object may be a robot hand or a walking assistance device.

In a wearable device for assisting a human body movement according to an embodiment of the present disclosure having a configuration as described above, deformation elements whose resistances are changed due to deformation are arranged long in a radial direction between an inner electrode disposed at the center of a circle and outer electrodes arranged at equal intervals on the circumference of the circle, and thus a combination value of the deformation elements corresponding to movements of a specific part of a human body is derived differently. Therefore, a single sensor may precisely sense deformation of muscles or skin moving in various directions, and the sensor is organically combined with a controller and an actuator mounted on the wearable device so that an exercise assistance or boost function using the wearable device may be implemented even with a simple configuration.

DETAILED DESCRIPTION

In the following description, in order to clarify the understanding of the present disclosure, descriptions of well-known technologies for the features of the present disclosure will be omitted. The following embodiment are detailed descriptions to help the understanding of the present disclosure, and it will be understood that the scope of the present disclosure is not limited. Accordingly, an equivalent invention that performs the same function as the present disclosure will also fall within the scope of the present disclosure.

In addition, in the following description, the same reference numerals or symbols means the same configuration, and unnecessary redundant description and description of known technology will be omitted. Moreover, a description of each embodiment of the present disclosure that overlaps with the description of the technology that is the background of the present disclosure will also be omitted.

A wearable device for assisting a human body movement, according to an embodiment of the present disclosure, will now be described in detail with reference to the accompanying drawings.

Figure 1:
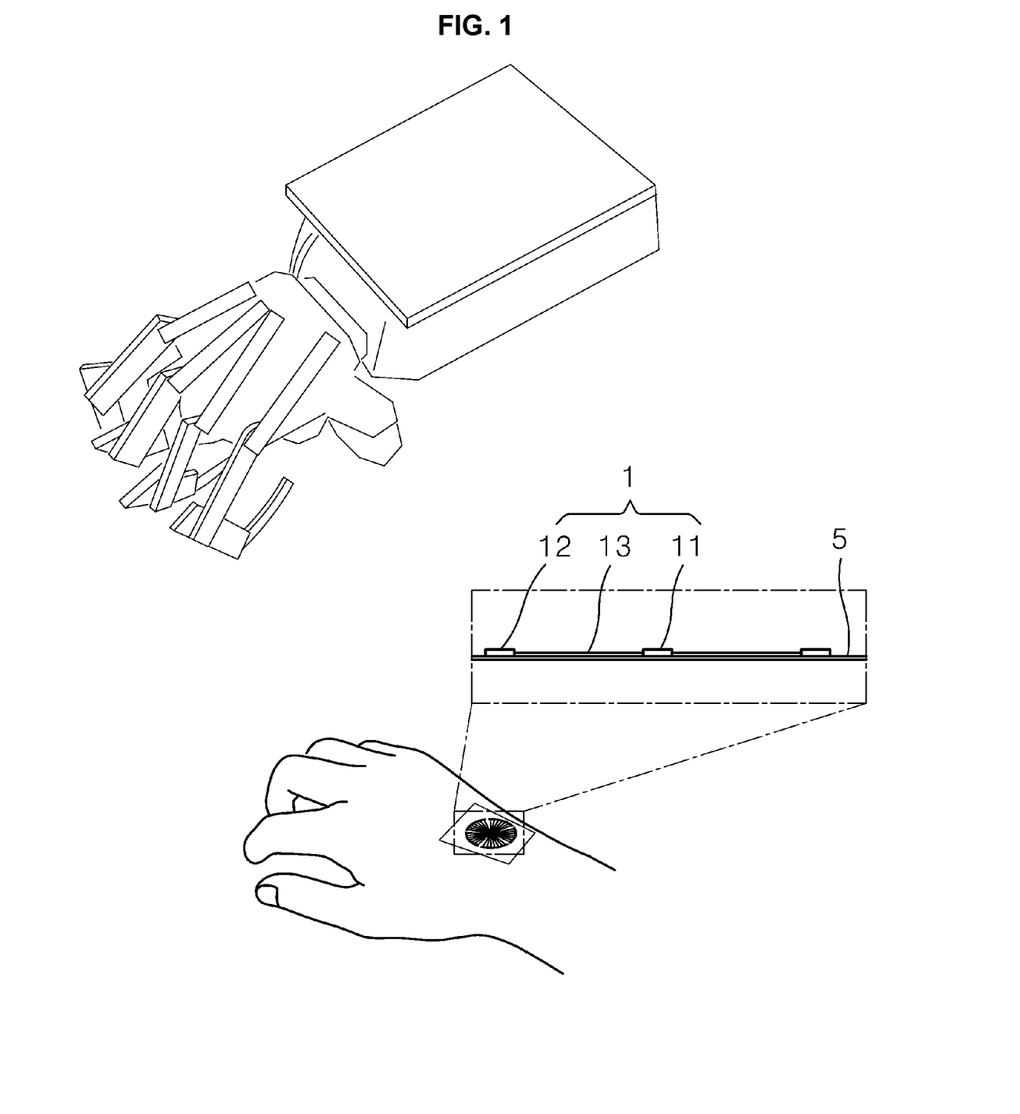
FIGS. 1 and 2 are views for explaining a wearable device for assisting a human body movement, according to an embodiment of the present disclosure.
Figure 2:
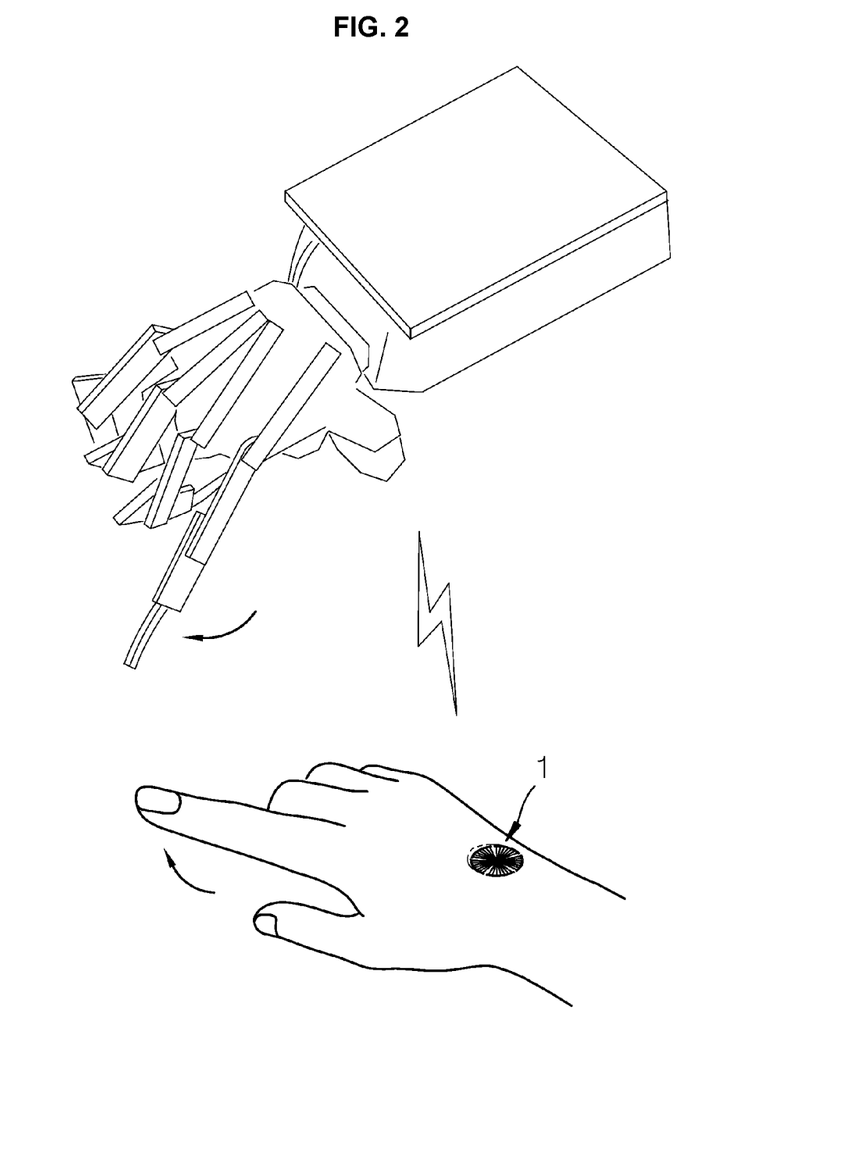
Figure 3:
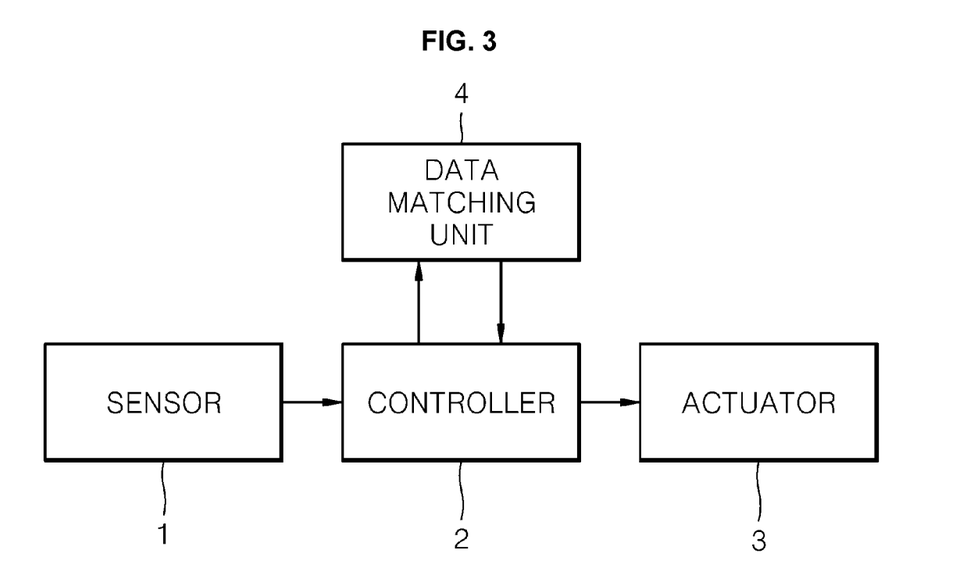
FIG. 3 is a block diagram for explaining a structure of an embodiment of the present disclosure.
Figure 4:
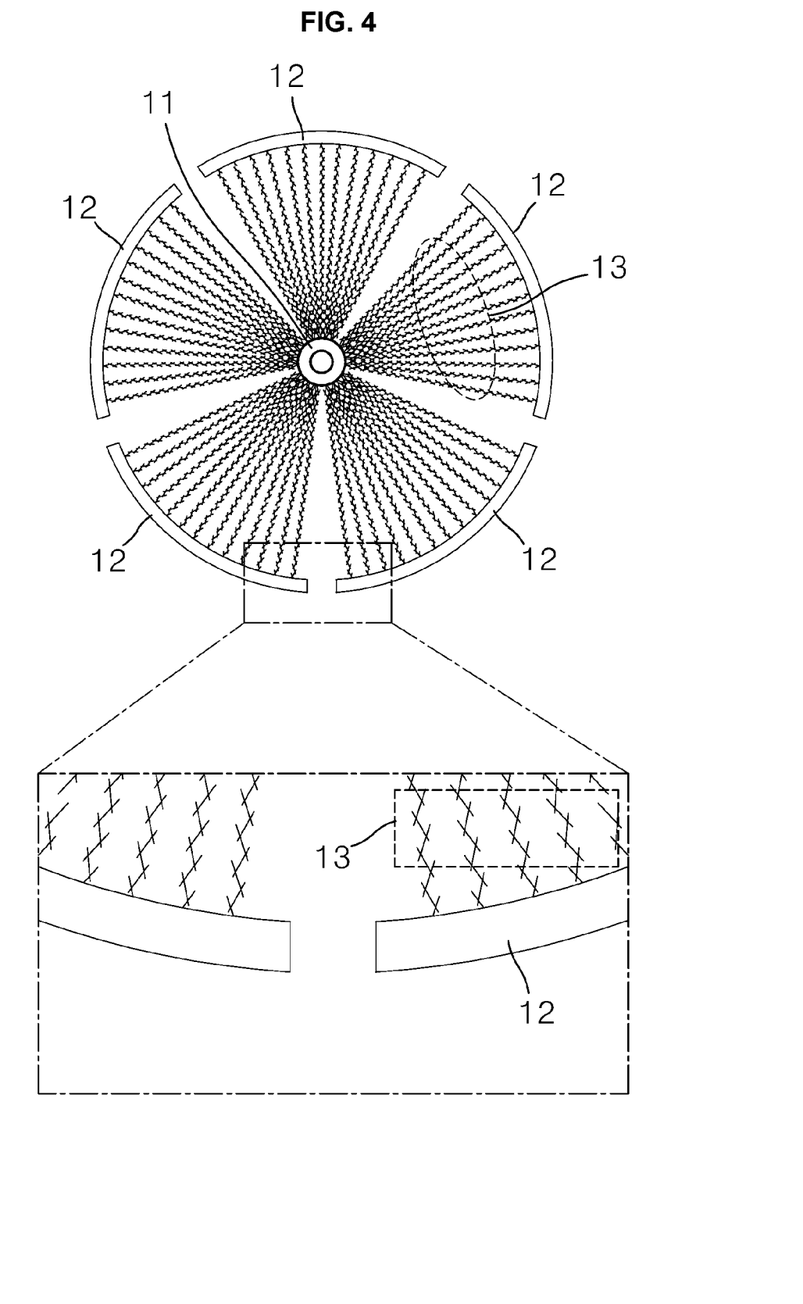
FIG. 4 is a view for explaining a structure of a sensor employed in an embodiment of the present disclosure.
Figure 5:
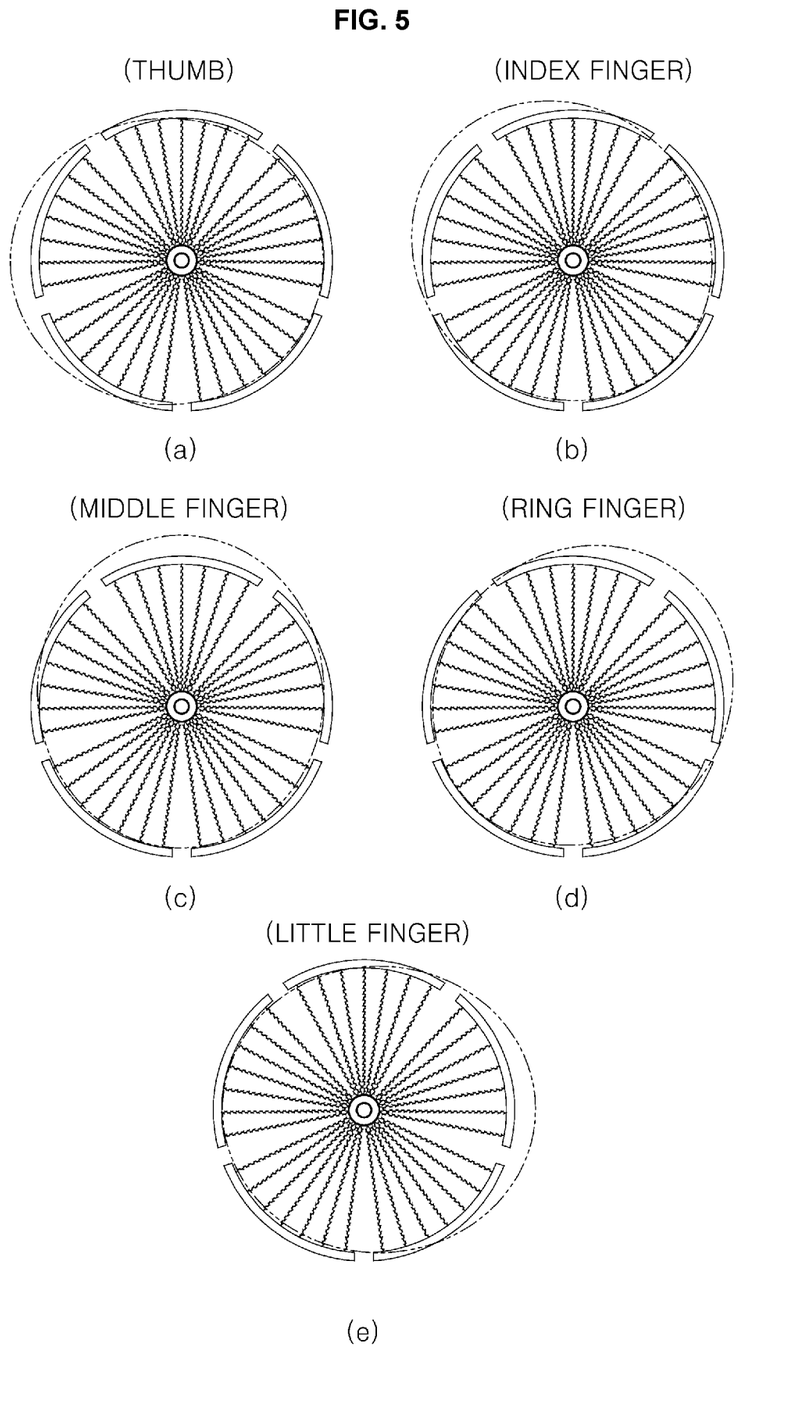
FIG. 5 is a view for explaining various modifications of a sensor employed in an embodiment of the present disclosure.
Figure 6:
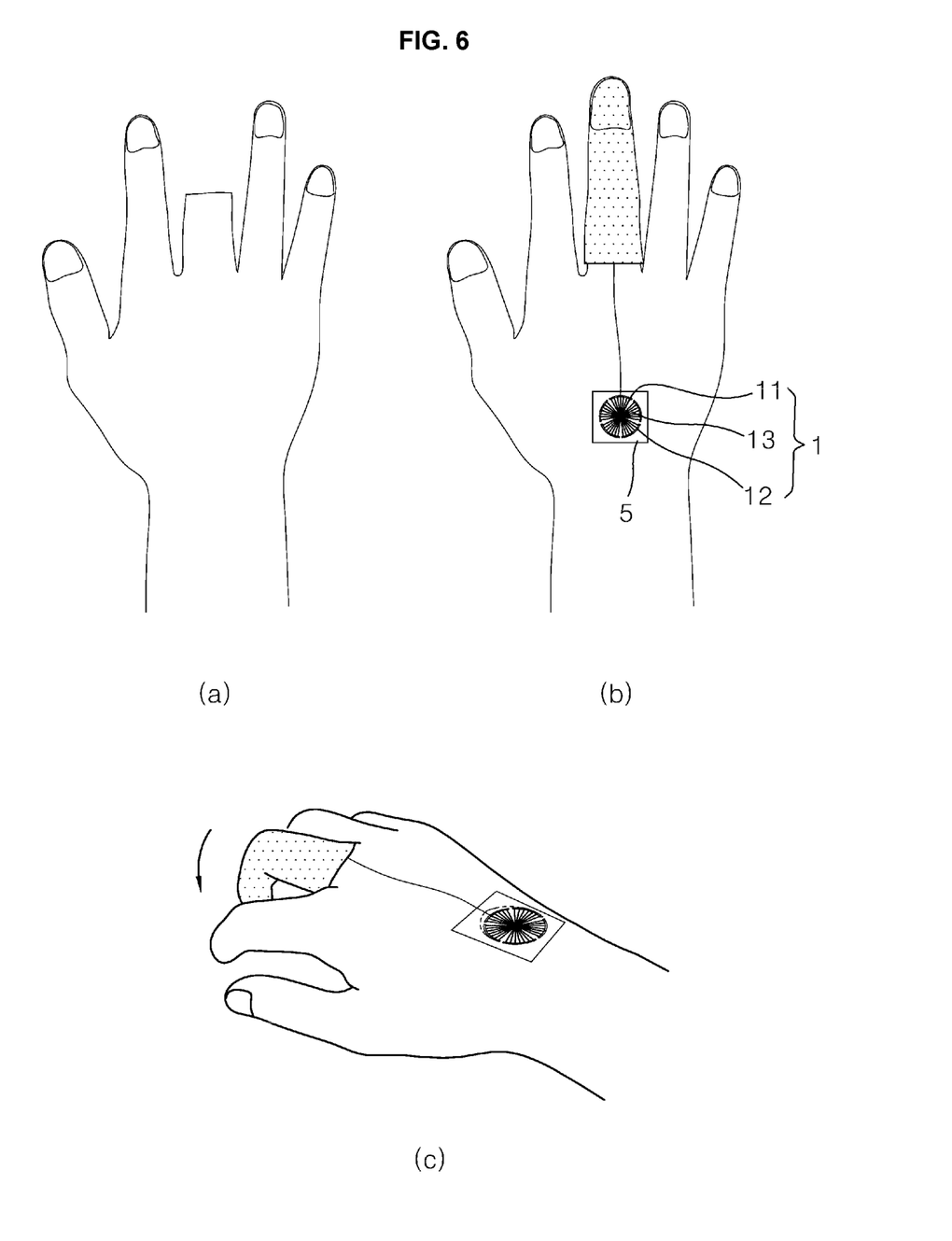
FIGS. 6 and 7 are views for explaining examples of use of an embodiment of the present disclosure.
Figure 7:
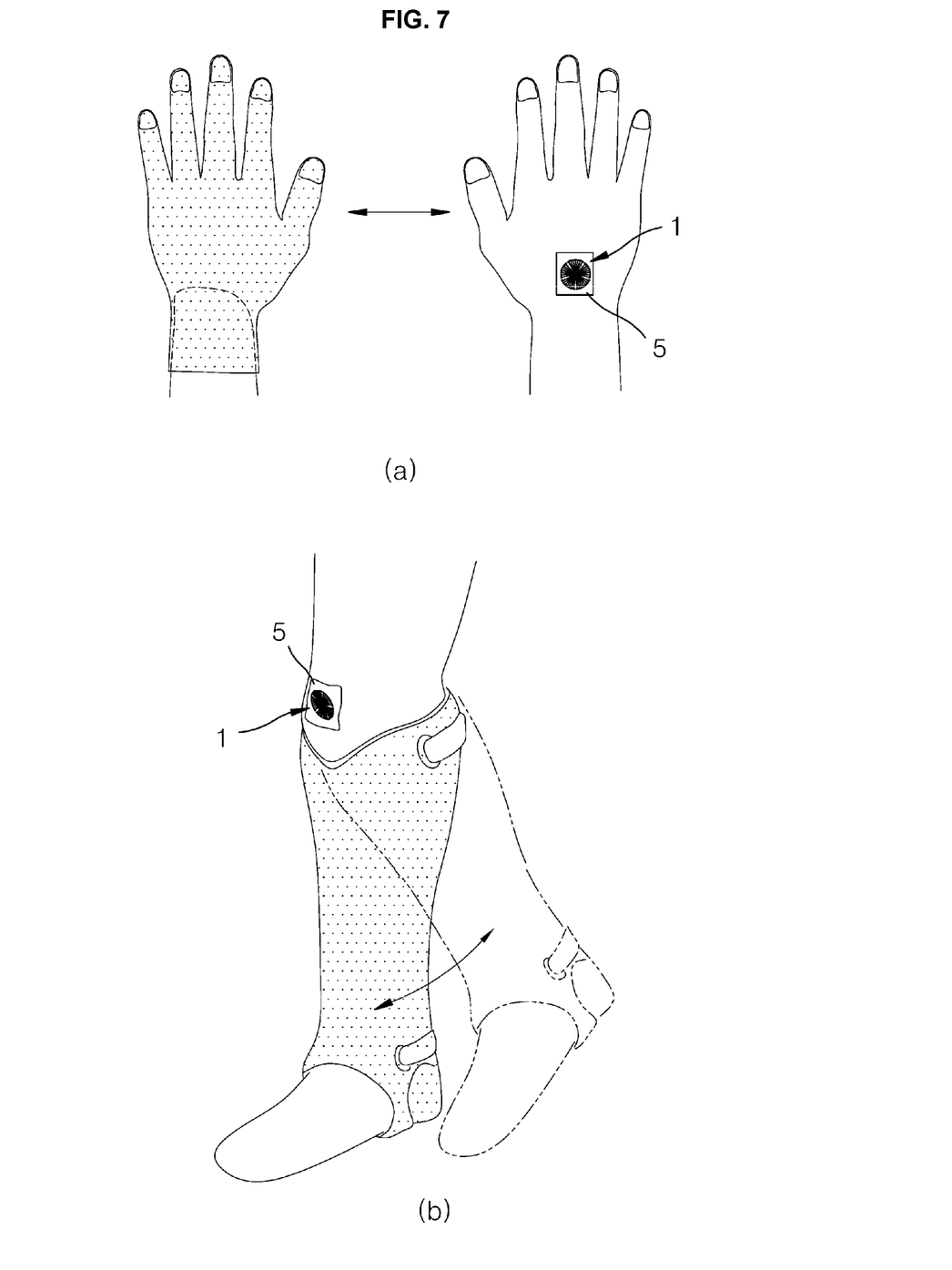

FIGS. 1 and 2 are views for explaining a wearable device for assisting a human body movement, according to an embodiment of the present disclosure, FIG. 3 is a block diagram for explaining a structure of an embodiment of the present disclosure, FIG. 4 is a view for explaining a structure of a sensor employed in an embodiment of the present disclosure, FIG. 5 is a view for explaining various modifications of a sensor employed in an embodiment of the present disclosure, and FIGS. 6 and 7 are views for explaining examples of use of an embodiment of the present disclosure.

As shown in FIGS. 1 through 3, the wearable device for assisting a human body movement, according to an embodiment of the present invention, may detect a complex and subtle muscle or skin movement state even by one sensor 1 and may help a specific movement of a body, such as a hand or a leg, based on a signal corresponding to a result of the detection, and includes the sensor 1, a controller 2, and an actuator 3.

As shown in FIG. 4, the sensor 1 is attached to, for example, a specific part of a human body and has different resistance values according to deformation of the corresponding part, and includes an inner electrode 11, outer electrodes 12, and deformation elements 13.

The inner electrode 11 is a part for measuring a change in resistance according to deformation of the deformation elements 13 together with the outer electrodes 12, and is arranged at the center of an arbitrary circle to be separated from the outer electrodes 12 to form a space in which the deformation elements 13 are placeable.

The outer electrodes 12 are arranged in a circumferential direction at positions spaced apart from the inner electrode 11 in a radial direction so as to be arranged on the circumference of the circle.

Each of the deformation elements 13 is disposed between the inner electrode 11 and each of the outer electrodes 12, and is formed of a material whose resistance is changed by deformation, such as carbon nanotubes (CNT).

Carbon nanotubes that provide structural stability, such as not being easily fractured by repeated deformation because of their high tensile strengths and high modulus of elasticity, and are capable of sensing even minute deformation in a specific direction because of their easy arrangement in one direction, may be employed as each of the deformation elements 13. However, the present disclosure is not limited thereto, and, for example, a fiber structure formed by combining a material such as polydimethylsiloxane (PDMS) elastomer capable of elastic deformation with a material having high electrical conductivity such as silver nanowire (AgNW) may be employed as each of the deformation elements 13.

The controller 2 applies different control signals to the actuator 3 according to a combination of changed resistance values of the deformation elements 13 of the sensor 1.

In other words, as shown in FIG. 5, when the sensor 1 is attached to the back of the hand and five fingers move, respective behavior characteristics of the five fingers are different from one another. Thus, when the outer electrodes 12 are five electrodes, five deformation elements 13 placed between the five electrodes and the inner electrode 11 have different resistance values corresponding to the respective behaviors of the five fingers.

For example, when a thumb among the five fingers moves ((a) of FIG. 5) and a middle finger ((c) of FIG. 5) moves, the five deformation elements 13 have different resistance values, and, when a combination of these resistance values is obtained in advance through an experiment and then the resistance value of the sensor 1 due to an actual finger movement through a software design matches with data obtained in advance through an experiment within a tolerance (comparison in a data matching unit 4 of FIG. 3), the controller 2 enables a control signal to be applied to the actuator 3 of the wearable device that helps the corresponding finger movement. Thus, as in the present embodiment, a wearable device that assists the movement of a specific part of a human body may be realized.

As such, the present embodiment includes an object driven by the actuator 3, and the object may be a variety of wearable devices worn on a specific part of the human body, for example, a robot hand (see FIG. 6 and (a) of FIG. 7) or a walking aid (see (b) of FIG. 7).

When the object driven by the actuator 3 is a robot hand, and the present embodiment is attached to a person having some difficulty in finger movement as shown in (a) of FIG. 6 and used as shown in (b) of FIG. 6, complete finger movement may be realized as shown in (c) of FIG. 6. When a prosthetic hand has to be worn because there is no left hand, as shown in (a) FIG. 7, the sensor 1 employed in the present embodiment is attached to the back of the right hand and the controller 2 and the actuator 3 are mounted and used on the left prosthetic hand, and thus the prosthetic hand simulates the behavior of the right finger to assist the movement of the left hand. According to this principle, as shown in (b) of FIG. 7, the present embodiment may also be utilized as a walking assistance device. As described above, the present embodiment may detect movements of joints such as fingers, wrists, and legs by measuring deformation of muscles or skin connected to the joints, and thus may be used in devices that assist movements or enhance related movements by grasping the intention of a person.

The present disclosure is not limited to the above-described robot hands or walking assistance devices, and may be utilized for various other purposes.

In other words, according to another embodiment of the present disclosure, the sensor may be attached to a part of the human body and the controller and the actuator may be mounted on an electronic device provided at a remote position from the human body, so that the actuator of the electronic device may operate according to a sensing value transmitted by the sensor according to a body movement of a user.

For example, according to another embodiment of the present disclosure, a part of the human body may be the back of a hand, and, when the electronic device is a robot hand or a robot glove worn by another person and a user with a sensor attached to the back of his or her hand acts to pet a puppy, the sensor detects the movement of this hand so that the robot hand placed at a distance or the robot glove worn by the other person may pet the puppy, and, when the electronic device is an illumination switch, remote illumination control may be performed only with a movement of the human body.

In addition, the present disclosure may be utilized to implement a smart home system like the above-described remote illumination control, and may also be utilized to implement a robot system that enables more delicate and sophisticated work on behalf of a user by installing a passive robot device having a multi-functional robot hand in a house and freely and remotely controlling and driving the robot hand like a real hand.

In the wearable device for assisting a human body movement, according to an embodiment of the present disclosure, having a configuration as described above, the deformation elements 13 whose resistances are changed due to deformation are arranged to each extend in the radial direction between the inner electrode 11 disposed at the center of the circle and the outer electrodes 12 arranged at equal intervals on the circumference of the circle, and thus a combination value of the deformation elements 13 corresponding to movements of a specific part of the human body is derived differently. Therefore, the single sensor 1 may still precisely sense deformation of muscles or skin moving in various directions, and the sensor 1 is organically combined with the controller 2 and the actuator 3 mounted on the wearable device so that an exercise assistance or boost function using the wearable device may be implemented even with a simple configuration.

The sensor 1 may further include a base member 5 which is attached to the human body and on which the inner electrode 11, the outer electrodes 12, and the deformation elements 13 are placed.

The base member 5 may be implemented with various materials, but may be preferably formed of a material that is elastically deformable, such as PDMS, so that the base member 5 may be restored to its original shape after deformation.

The present disclosure is not limited to a method of fixing a sensor by using the base member 5, and may be configured such that a sensor may be fixed to the skin of a human body with only the structure of the sensor itself without a medium such as the base member 5. In other words, when the sensor 1 is fixed to a transfer film (not shown) and attached to a skin, the inner electrode 11, the outer electrodes 12, and the deformation elements 13 that form the sensor structure are transferred from the transfer film to the skin, and thus the sensor 1 may be fixed to the skin with only its own structure without a medium for adhesion to the skin.

Of course, such sensor transfer may be implemented in various structures. For example, one surface of the inner electrode 11 and respective one surfaces of the outer electrodes 12 are attached to the transfer film with a weak bonding force, and the other surface of the inner electrode 11 and the respective other surfaces of the outer electrodes 12 facing the skin have a stronger bonding force than the one surfaces thereof, and thus the sensor employed in the present embodiment may be smoothly transferred from the transfer film to the skin.

Each of the deformation elements 13 may be a CNT unit in which CNT monomers are connected to each other. In other words, as described above, the CNT provide structural stability, such as not being easily fractured by repeated deformation because of their high tensile strengths and high modulus of elasticity, and are capable of sensing even minute deformation in a specific direction because of their easy arrangement in one direction.

Each CNT monomer may include a conductive material enabling different values to be output according to deformation of an impedance value (or a resistance value).

Although the conductive material may be implemented with various materials, it is preferable that the conductive material may include PEDOT:PSS to improve response characteristics to deformation. In other words, the PEDOT:PSS effectively transfers charges within the CNT monomers by maintaining conductivity even when the CNT monomers are disconnected from one another due to deformation.

Although various embodiments of the present disclosure have been described above, the present embodiment and the drawings attached to this specification only clearly show a portion of the technical idea included in the present disclosure, and it will be apparent that all modifications and specific embodiments that can be easily inferred by those skilled in the art within the scope of the technical spirit included in the drawings included in the specification and drawings of the present disclosure are included in the scope of the present disclosure.

What is claimed is:

1. A wearable device for assisting a human body movement, the wearable device comprising:
    a sensor comprising an inner electrode arranged at a center of an arbitrary circle, a plurality of outer electrodes arranged at regular intervals in a circumferential direction at positions spaced apart from the inner electrode in a radial direction so as to be arranged on a circumference of the circle, and a plurality of deformation elements disposed between the inner electrode and each of the outer electrodes and formed of a material whose resistance is changed by deformation;
    a controller configured to apply different control signals to an actuator according to a combination of different resistance values of the deformation elements of the sensor; and
    the actuator operating based on the control signals of the controller.

2. The wearable device of claim 1, wherein the sensor further comprises a base member which is attached to a human body and on which the inner electrode, the outer electrodes, and the deformation elements are placed.

3. The wearable device of claim 1, wherein the sensor is attached to a skin of a human body by a transfer method to be fixed to the skin with only a structure of the sensor without a medium for attachment to the skin.

4. The wearable device of claim 1, wherein each of the deformation elements is a carbon nanotube (CNT) unit in which CNT monomers are connected to each other.

5. The wearable device of claim 1, further comprising an object driven by the actuator, wherein the object is robot hands.

6. The wearable device of claim 1, further comprising an object driven by the actuator, wherein the object is a walking assistance device.

7. The wearable device of claim 1, wherein the sensor is attached to part of a human body, and the controller and the actuator are mounted on an electronic device provided at a remote position from the human body, so that the actuator of the electronic device operates according to a sensing value transmitted by the sensor according to a body movement of a user.

* * * * *